United States Patent [19]
Boniuk

[11] 3,979,780
[45] Sept. 14, 1976

[54] INTRAOCULAR LENS AND SUPPORTING SYSTEM THEREFOR

[75] Inventor: Vivien Boniuk, New York, N.Y.

[73] Assignee: Revlon, Inc., New York, N.Y.

[22] Filed: Apr. 7, 1975

[21] Appl. No.: 565,505

[52] U.S. Cl. ................................................ 3/13
[51] Int. Cl.² ...................... A61F 1/16; A61F 1/24
[58] Field of Search .................... 3/13, 1; 351/160

[56] References Cited
UNITED STATES PATENTS

| | | | |
|---|---|---|---|
| 3,673,616 | 7/1972 | Fedorov et al. | 3/13 |
| 3,866,249 | 2/1975 | Flom | 3/13 |

OTHER PUBLICATIONS
"Intra-Ocular Acrylic Lenses After Cataract Extraction" by Harold Ridley, *The Lancet*, Jan. 19, 1952, pp. 118–121.

Primary Examiner—Ronald L. Frinks
Attorney, Agent, or Firm—Rogers, Bereskin & Parr

[57] ABSTRACT

An artificial intraocular lens of the type intended for placement in the anterior chamber of the eye between the cornea and the iris to enable the eye to focus images upon the retina wherein the lens is supported by means of supporting members such as loops and struts extending both posteriorly and anteriorly of the iris when the lens is in place, the supporting members having inter-connected portions which extend through apertures in the lens, the clearance between the apertures and the portions of the supporting members in the apertures being substantial so that the lens is held by the supporting members without any rigid connection between the supporting members and the lens.

12 Claims, 4 Drawing Figures

INTRAOCULAR LENS AND SUPPORTING SYSTEM THEREFOR

This invention relates to the art of ophthalmology and in particular to an improved artificial intraocular lens of the type intended for placement in the anterior chamber of the eye between the cornea and the iris.

When the natural lens of the eye is removed, for example, to correct a cataract condition, it is necessary to provide an artificial lens to enable the eye to focus images on the retina. Commonly, corrective lenses are mounted in spectacle frames. Many ophthalmologists are unsatisfied with such an arrangement, however, because such spectacle lenses tend to restrict peripheral vision and perfect binocular vision is sometimes difficult to achieve. In addition, such spectacle lenses tend to be quite heavy and many people find them unattractive as the power of the lenses is such that they tend to distort the appearance of the eye.

Early attempts at artificial lens implants in the eye to replace the natural lens of the eye were not very satisfactory in that the lenses frequently became dislodged and damaged the eye, or had to be repositioned in another operation. Originally, the artificial lenses were placed in the eye without any means of preventing migration of the lenses, and this was soon found to be very unsatisfactory. More recently, it has become common practice to provide artificial lenses having posterior loops which are inserted behind the iris and which extend radially outwards to limit the anterior travel of the lens, and loops or struts extending from the periphery of the lens and which are positioned in front of the iris to prevent posterior migration of the lens. An example of this type of lens is shown in U.S. Pat. No. 3,673,616 of S. N. Federov, dated July 4, 1972.

Conventional artificial implant lenses of the kind referred to above are commonly made of methyl methacrylate resins on the theory that methyl methacrylate is inert in the eye and hence will not tend to produce complications in the eye. An advantage of methyl methacrylate is that its density is fairly close to that of water and therefore a lens made of methyl methacrylate has comparatively little weight in the aqueous humour which fills the anterior chamber of the eye.

The use of lenses of synthetic resin such as methyl methacrylate has not, however, been a completely satisfactory solution for a number of reasons. First, the supporting loops and struts which commonly are made of nylon, are fixed to the lens by firstly drilling small holes in the lens, heating the lens to slightly enlarge the openings and then embedding the ends of the loops and struts in the holes, so that upon cooling, the holes in the lens will tend to contract and firmly hold the ends of the loops and struts. The operations of drilling and heating the lenses inevitably lead to some degree of contamination of the lenses, a condition which in the case of a plastic lens cannot be cured by heating, and moreover it is not a rare occurrence for the struts to become dislodged from the lens. In addition, the junction of the struts or loops and the lens tends to provide a site for inflammatory material such as bacteria, cell debris, and the like.

Another complication which results from the use of artificial intraocular lenses is pupillary block. The lens tends to impede the natural flow of aqueous humour from the posterior to the anterior side of the iris. In order to overcome this problem, it is common practice to perform a peripheral iridectomy when implanting the lens, i.e. to make a small hole in the iris near the outer edge thereof to facilitate the flow of aqueous humour. This procedure is usually successful in preventing pupillary block but nevertheless complications do occasionally arise when the hole in the iris becomes obstructed.

In view of problems such as those referred to above, it would clearly be desirable to use lenses made of a material which is substantially inert, which is designed so that it does not tend to trap inflammatory material, and which avoids the problem of pupillary block. An excellent material in this respect is glass which can be made of materials which are substantially inert in the eye. However, although the use of glass in artificial lens implants of the kind referred to above has previously been proposed, no completely satisfactory arrangement has ever been devised for supporting a glass lens inside the eye. One of the main reasons for this is that glass is quite heavy compared with methyl methacrylate, and conventional supporting systems of the kind used with methyl methacrylate lenses were not considered feasible with glass.

The problems referred to above have been overcome in the present invention which, although it can be applied to advantage in conventional lenses of synthetic resins such as methyl methacrylate, is particularly suited for use with lenses of glass. In the present invention, apertures are formed in the lens by drilling or any other conventional means. A piece of wire used to form the supporting loops and struts is threaded through the apertures and emerges at appropriate locations in the lens, the exposed portions of the wire being shaped to form the loops and struts. The free ends of the wire are welded together, so that the supporting system is of a unitary nature and is not rigidly connected to the lens, as in the case of the supporting systems used in the prior art. Moreover, by providing a generous clearance between the walls of the apertures in the lens and the supporting wires in the apertures, the aqueous humour is permitted to circulate through the lens thus considerably reducing the possibility of build up of inflammatory material on or in the lens. In addition by providing at least one aperture which extends through the lens from the anterior to the posterior side, there is provided a conduit for aqueous to enable the aqueous to flow through the pupil from the posterior side of the lens to the anterior side of the lens, thus substantially reducing the risk of pupillary block due to the presence of the lens in front of the iris.

Objects of the present invention are therefore to provide an inert lens which minimizes the risk of irritation or other undesirable complications when implanted in the eye, and which minimizes the risk of pupillary block. Other objects and advantages of the present invention will become apparent from the following specification and drawings in which.

Figure 4:
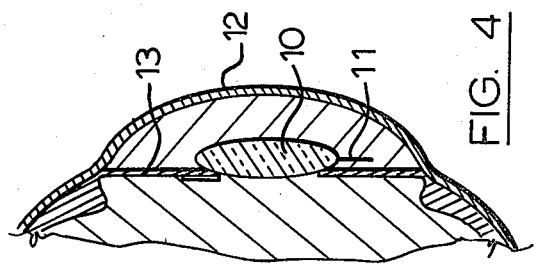
FIG. 4 is a sectional view taken along the line 4—4 of FIG. 1, with the lens in place in the eye.
Figure 1:
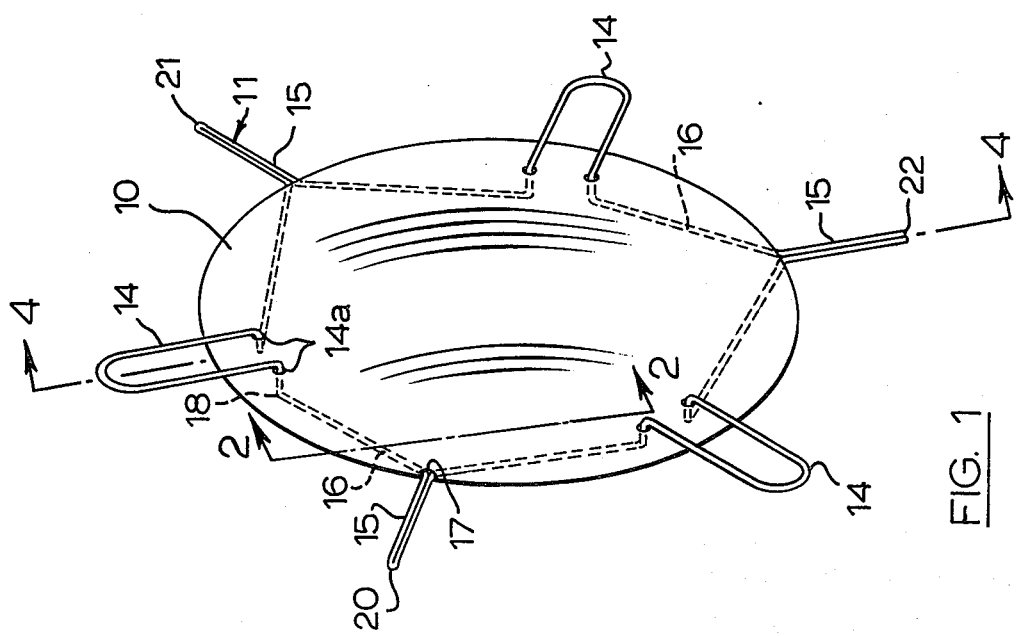
FIG. 1 is a perspective view showing a preferred embodiment of the present invention.

Referring to the drawings, and in particular to FIG. 1, a preferred form of intraocular lens according to the invention includes an artificial lens 10 and a supporting system 11 which is intended to maintain the lens in the position shown in FIG. 4, wherein the lens is positioned in the anterior chamber of the eye between the cornea 12 and the iris 13.

Figure 2:
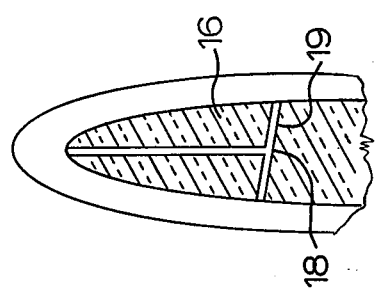
FIG. 2 is a sectional view taken along the line 2—2 of FIG. 1 with the supporting wires removed.

The supporting system 11 is preferably formed from a single piece of inert, resilient material, which is non-irritating to the eye, preferably a noble metal such as platinum, iridium and the like, and which is shaped to form three equiangularly spaced loops 14 and three equiangularly spaced struts 15 which respectively are positioned mid-way between adjacent loops 14, as shown in FIG. 1. The wire forming the loops 14 and the struts 15 is threaded through apertures 16 and 19 which are formed in the lens 10, as shown in FIGS. 1 and 2. The apertures 16 and 19 may be produced by any conventional means such as laser drilling. Each aperture 16 extends from a point 17 at or near the periphery of the lens 10 to a point 18 which is located inside the lens 10 in line with inner end 14a of a loop 14. The apertures 16 communicate with the apertures 19 which preferably extend from the posterior to the anterior side of the lens 10 and the apertures 19 preferably are inclined relative to the optical axis of the lens 10 as shown in FIG. 2, to facilitate threading the wire.

The inner ends 14a of the loops 14 are positioned a substantial distance inwardly from the periphery of the lens 10 so that the inner ends 14a do not substantially impede the iris when the eye is exposed to bright light. In addition, the inner ends 14a of the loops are shaped to space the loops 14 posteriorly from the adjacent or posterior surface of the lens 10, as shown in FIG. 4, to enable the loops 14 to be inserted in place behind the iris 13. The loops 14 extend radially outwards as shown in FIGS. 1 and 4 and they are of a sufficient length so that when they are in place, they tend to prevent the lens from moving any substantial distance towards the cornea even when the eye is in darkness and the pupil is dilated to its maximum extent.

The struts 15 extend radially outwards from the periphery of the lens and they are of approximately the same radial extent as the loops 14. The struts 15 are formed by bending the wire of which they are made through a small radius as at 20 and 21. The free ends of the wire meet at 22 and it is convenient to weld the ends of the wire together at this point, following which the welded end of the relevant strut 15 should be smoothed to remove any sharp projections or irregularities.

The platinum wire of which the supporting system 11 is made is preferably of a diameter of about 10 – 30 microns and the diameter of the apertures 16 and 19 is between about 10 to 40% greater than the diameter of the wire, 25% greater being preferred. By allowing a fairly generous clearance between the portion of the wire which is in the apertures 16 and 19 and the walls of the apertures 16 and 19, aqueous is permitted to flow quite freely through the apertures 16 and 19 and hence tends to flush out any bacteria, cell debris, etc. which might tend to accumulate in the apertures 16 and 19. In addition, by permitting the aqueous humour to flow through one or more apertures 19 from the posterior to the anterior side of the lens, the likelihood of pupillary block substantially is reduced.

Although the lens 10 may be composed of any inert optical material commonly used in the manufacture of intraocular lenses such as methyl methacrylate, the present invention is particularly suitable for use with a glass lens. The glass must be made with materials which are non-toxic and preferably the glass has a neutral pH.

It is desirable to make the lens as thin as possible consistent with the power necessary. The power of the lens 10, in accordance with conventional practice, is selected to correspond with the power of the cornea of the eye being treated and the length of said eye, to enable the eye with the lens in position in the eye to focus images on the retina.

Figure 3:
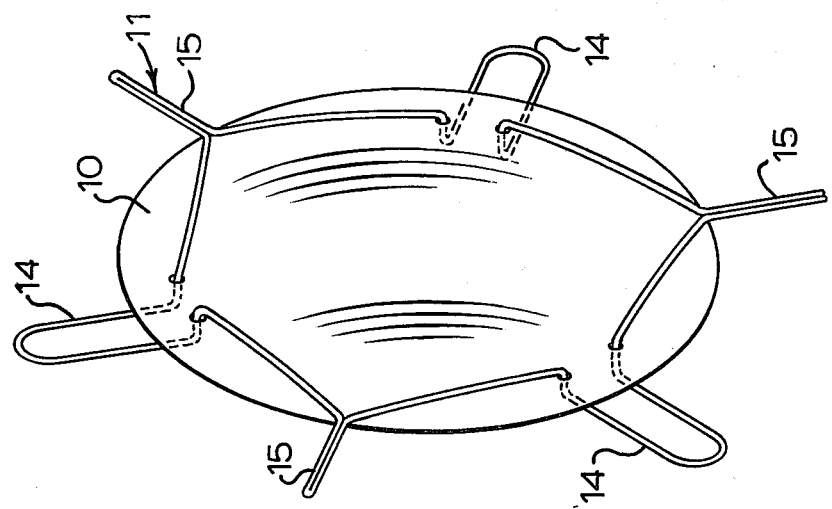
FIG. 3 is a perspective view illustrating another embodiment of the invention.

The embodiment shown in FIG. 3 is similar to the embodiment of FIG. 1 in terms of the configuration of the supporting system 11, but it differs from that of FIG. 1 in that there are no apertures 16 extending inwardly into the lens 10. Instead, the apertures 19 are drilled through the lens from the anterior to the posterior sides, and the portions of the wire of the supporting system 11 which interconnect the loops 14 and the struts 15 are positioned on the outside surface of the lens 10. In view of the small diameter of the wire and its position, the wire will be invisible to the eye. It is preferable to spot weld each of the struts 15 near the periphery of the lens 10 to minimize the possibility of the wire spreading apart at this point.

Although the invention has been described above with reference to a supporting system comprising three posterior loops and three anterior struts, it will be understood that principles of the invention may be applied to other types of supporting systems as well, such as the type wherein there are two posterior loops and two anterior loops, or the type where there are only anterior struts, the lens being positioned posteriorly of the iris.

What I claim is:

1. In an artificial intraocular lens of the type intended for placement in the anterior chamber of the eye between the cornea and the iris the enable the eye to focus images upon the retina, said lens being supported by means of inert, resilient, wire-like supporting members extending both radially outwards of the lens, the improvement wherein said supporting members have portions which extend through apertures in the lens, said supporting member portions being inter-connected, and wherein the clearance between said apertures and said supporting member portions is substantial, so that the lens is held by the supporting members without any rigid connection between the supporting members and the lens, whereby aqueous humour is able to freely pass through the apertures when the lens is in place.

2. The invention as claimed in claim 1 wherein said apertures are of circular cross-section, wherein the supporting members extend both posteriorly and anteriorly of the iris when the lens is in place, and wherein the diameter of said apertures is between about 10 – 30% greater than the diameter of said supporting members.

3. The invention as claimed in claim 1 wherein at least one of said apertures extends through the lens from the posterior to the anterior side thereof.

4. The invention as claimed in claim 1 wherein said apertures are of circular cross-section, wherein the diameter of said apertures is between about 10 – 30% greater than the diameter of said supporting members, and wherein at least one of said apertures extends through the lens from the posterior to the anterior side thereof.

5. The invention as claimed in claim 1 wherein the supporting members are formed of a single piece of inert wire-like material the free ends of which are joined together.

6. The invention as claimed in claim 2 wherein the supporting members are formed of a single piece of inert wire-like material the free ends of which are joined together.

7. The invention as claimed in claim 3 wherein the supporting members are formed of a single piece of inert wire-like material the free ends of which are joined together.

8. The invention as claimed in claim 7 wherein the wire-like material is platinum.

9. The invention as claimed in claim 1 wherein said lens is of glass which is substantially inert in the eye.

10. An artificial intraocular lens for placement in the anterior chamber of the eye between the cornea and the iris, the lens having anterior and posterior surfaces and having an optical axis that is substantially aligned with the optical axis of the eye when the lens is in place, said lens having a predetermined optical power consistent with the optical power of the cornea of the eye and the length of the eye to permit the lens to focus images upon the retina of the eye, and a supporting system for said lens comprising a plurality of substantially equiangularly spaced generally coplanar loops extending radially outwards from the posterior side of said lens, each of said loops having inner ends which enter the lens through apertures in the lens, said apertures being spaced inwardly from the periphery of the lens to minimize interference with the iris, said inner ends being shaped to space said loops a predetermined distance from the posterior surface of said lens, and a plurality of struts extending radially outwards from the periphery of said lens, said struts being positioned anteriorly of said iris when said lens is in place, the radial extent of said loops and struts being such as to retain the lens in place when said iris has dilated to its maximum extent in darkness, said loops and struts being formed of inert, resilient wire-like material and said loops and struts being connected together to form a unitary supporting system, said loops and struts extending into said lens through apertures in said lens, the clearance between said apertures and the portion of said supporting system which is enclosed in said apertures being substantial so that the lens is held by said supporting system without any rigid connection between said supporting system and said lens.

11. The invention as claimed in claim 10 wherein at least one of said apertures extends through the lens from the posterior to the anterior side thereof.

12. The invention as claimed in claim 11 wherein at least one of said apertures extends from the posterior to the anterior side of the lens, wherein said apertures are of circular cross-section, and wherein the diameter of said apertures is between about 10 – 30% greater than the diameter of said supporting members.

* * * * *